(12) United States Patent
Becker et al.

(10) Patent No.: US 9,382,172 B2
(45) Date of Patent: Jul. 5, 2016

(54) PROCESS OF PRODUCING CYCLOHEXYLBENZENE

(71) Applicant: ExxonMobil Chemical Patents Inc., Baytown, TX (US)

(72) Inventors: Christopher L. Becker, Manhattan, KS (US); James R. Lattner, LaPorte, TX (US); Keith H. Kuechler, Friendswood, TX (US); Hari Nair, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 209 days.

(21) Appl. No.: 14/375,996

(22) PCT Filed: Dec. 5, 2012

(86) PCT No.: PCT/US2012/067974
§ 371 (c)(1),
(2) Date: Jul. 31, 2014

(87) PCT Pub. No.: WO2013/130153
PCT Pub. Date: Sep. 6, 2013

(65) Prior Publication Data
US 2015/0045596 A1    Feb. 12, 2015

Related U.S. Application Data

(60) Provisional application No. 61/605,266, filed on Mar. 1, 2012.

(30) Foreign Application Priority Data

Mar. 30, 2012  (EP) ..................................... 12162348

(51) Int. Cl.
*C07C 2/74* (2006.01)
*C07C 2/54* (2006.01)
(Continued)

(52) U.S. Cl.
CPC . *C07C 2/74* (2013.01); *C07C 5/367* (2013.01); *C07C 2529/08* (2013.01); *C07C 2529/18* (2013.01); *C07C 2529/70* (2013.01); *C07C 2529/89* (2013.01)

(58) Field of Classification Search
None
See application file for complete search history.

(56) References Cited

U.S. PATENT DOCUMENTS 3,354,078 A    11/1967   Miale et al.
4,094,918 A     6/1978   Murtha et al.
(Continued)

FOREIGN PATENT DOCUMENTS

EP    0 293 032       11/1988
WO    WO 97/17290      5/1997
(Continued)

OTHER PUBLICATIONS

Miale, "*Catalysis by Crystalline Aluminosilicates—IV. Attainable Catalytic Cracking Rate Constants, and Superactivity*", Journal of Catalysis, vol. 6, pp. 278-287, 1966.
(Continued)

*Primary Examiner* — In Suk Bullock
*Assistant Examiner* — Philip Louie
(74) *Attorney, Agent, or Firm* — Stephen A. Baehl

(57) ABSTRACT

In a process for producing cyclohexylbenzene, benzene is contacted with hydrogen in the presence of a hydroalkylation catalyst under hydroalkylation conditions effective to form a first effluent stream comprising cyclohexylbenzene, cyclohexane, and benzene. At least a portion of the cyclohexane from the first effluent stream is then contacted with hydrogen in the presence of a dehydrogenation catalyst under dehydrogenation conditions effective to convert at least some of the cyclohexane into benzene contained in a second effluent stream. At least some of the hydrogen is supplied to the process so as to contact the dehydrogenation zone (e.g., the dehydrogenation catalyst) before contacting the hydroalkylation catalyst.

20 Claims, 1 Drawing Sheet

(51) Int. Cl.
    *C07C 7/04* (2006.01)
    *C07C 5/367* (2006.01)

(56) References Cited

U.S. PATENT DOCUMENTS

| | | | |
|---|---|---|---|
| 4,122,125 A | 10/1978 | Murtha et al. |
| 4,177,165 A | 12/1979 | Murtha et al. |
| 4,206,082 A | 6/1980 | Murtha et al. |
| 4,439,409 A | 3/1984 | Puppe et al. |
| 4,826,667 A | 5/1989 | Zones et al. |
| 4,954,325 A | 9/1990 | Rubin et al. |
| 5,053,571 A | 10/1991 | Makkee |
| 5,236,575 A | 8/1993 | Bennett et al. |
| 5,250,277 A | 10/1993 | Kresge et al. |
| 5,362,697 A | 11/1994 | Fung et al. |
| 6,037,513 A | 3/2000 | Chang et al. |
| 6,049,018 A | 4/2000 | Calabro et al. |
| 6,077,498 A | 6/2000 | Diaz Cabñas et al. |
| 6,720,462 B2 | 4/2004 | Kuhnle et al. |
| 6,756,030 B1 | 6/2004 | Rhode et al. |
| 7,579,511 B1 | 8/2009 | Dakka et al. |

FOREIGN PATENT DOCUMENTS

| | | |
|---|---|---|
| WO | WO 02/00341 | 1/2002 |
| WO | WO 2009/025939 | 2/2009 |
| WO | WO 2009/131769 | 10/2009 |
| WO | WO 2011/096990 | 8/2011 |

OTHER PUBLICATIONS

Weisz, *"Superactive Crystalline Aluminosilicate Hydrocarbon Catalysts"*, Journal of Catalysis, vol. 4, pp. 527-529, 1965.

Olson et al., *"Chemical and Physical Properties of the ZSM-5 Substitutional Series"*, Journal of Catalysis, vol. 61, pp. 390-396, 1980.

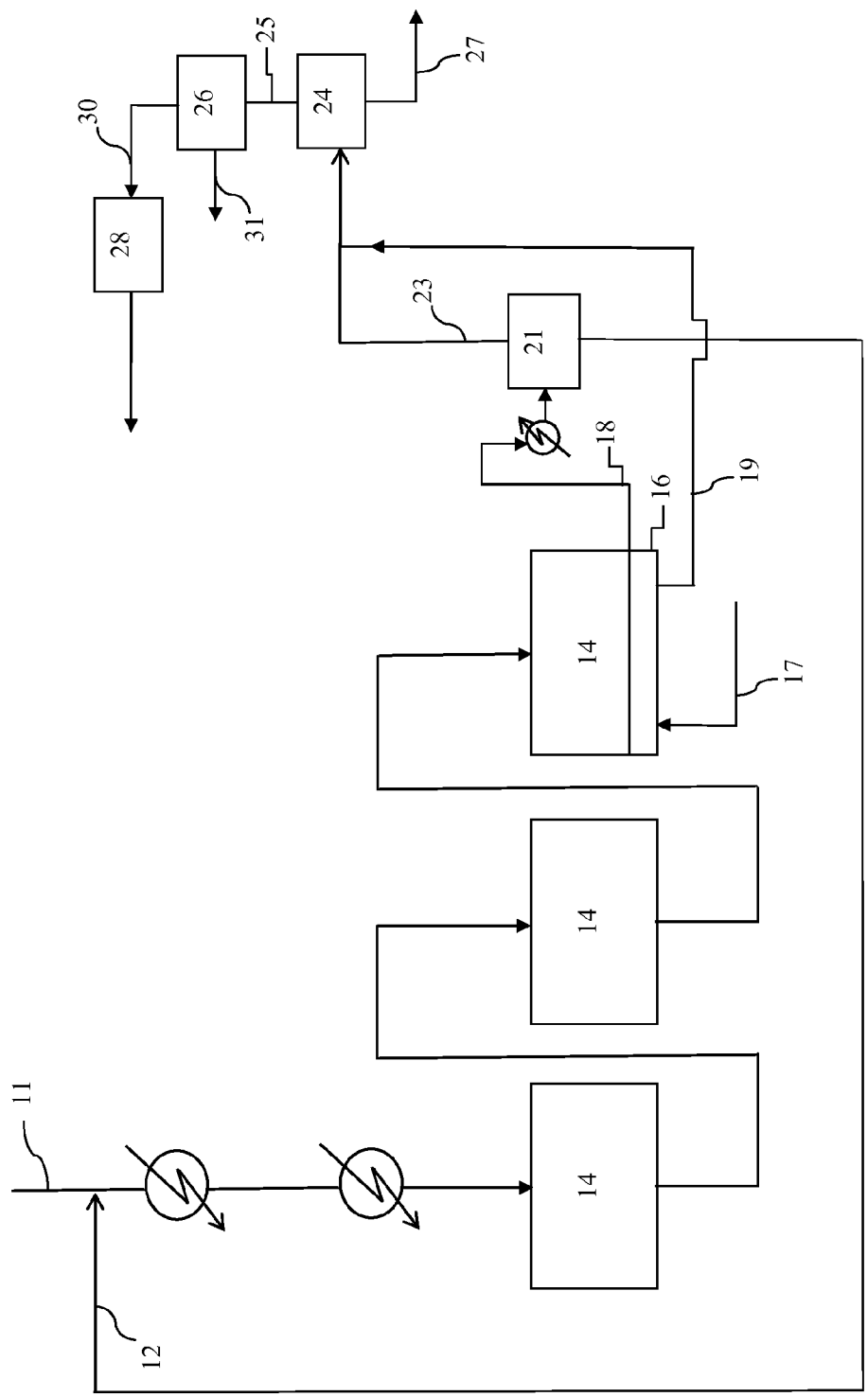

PROCESS OF PRODUCING CYCLOHEXYLBENZENE

PRIORITY CLAIM TO RELATED APPLICATIONS

This application is a National Stage Application of International Application No. PCT/US2012/067974 filed Dec. 5, 2012, which claims priority to U.S. Provisional Application Ser. No. 61/605,266 filed Mar. 1, 2012 and European Application No. 12162348.2 filed Mar. 30, 2012, the disclosures of which are fully incorporated herein by their reference.

FIELD

The present invention relates to a process for producing cyclohexylbenzene and to the use of the resultant cyclohexylbenzene in the production of phenol and cyclohexanone.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, due to a developing shortage, the cost of propylene is likely to increase. Thus, a process that uses higher alkenes instead of propylene as feed and co-produces higher ketones, rather than acetone, may be an attractive alternative route to the production of phenols.

One such process proceeds via cyclohexylbenzene, followed by the oxidation of the cyclohexylbenzene to cyclohexylbenzene hydroperoxide, which is then cleaved to produce phenol and cyclohexanone in substantially equimolar amounts.

Cyclohexylbenzene can be produced from benzene by the process of hydroalkylation or reductive alkylation. In this process, benzene is heated with hydrogen in the presence of a catalyst such that the benzene undergoes partial hydrogenation to produce a reaction intermediate such as cyclohexene which then alkylates the benzene starting material. Thus, U.S. Pat. Nos. 4,094,918 and 4,177,165 disclose hydroalkylation of aromatic hydrocarbons over catalysts which comprise nickel and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. In addition, U.S. Pat. No. 5,053,571 proposes the use of ruthenium and nickel supported on zeolite beta as the aromatic hydroalkylation catalyst. However, these earlier proposals for the hydroalkylation of benzene suffer from the problems that the selectivity to cyclohexylbenzene is low, particularly at economically viable benzene conversion rates, and that large quantities of unwanted by-products are produced.

More recently, U.S. Pat. No. 6,037,513 has disclosed that cyclohexylbenzene selectivity in the hydroalkylation of benzene can be improved by contacting the benzene and hydrogen with a bifunctional catalyst comprising at least one hydrogenation metal and a molecular sieve of the MCM-22 family. The hydrogenation metal is preferably selected from palladium, ruthenium, nickel, cobalt, and mixtures thereof, and the contacting step is conducted at a temperature of 50° C. to 350° C., a pressure of 100 kPa to 7000 kPa, a benzene to hydrogen molar ratio of 0.01 to 100 and a weight hourly space velocity (WHSV) of 0.01 $hr^{-1}$ to 100 $hr^{-1}$. The '513 patent discloses that the resultant cyclohexylbenzene can then be oxidized to the corresponding hydroperoxide and the peroxide decomposed to the desired phenol and cyclohexanone.

Although the process of the '513 patent represents a significant improvement over earlier processes for the hydroalkylation of benzene, it still suffers from the problem that significant properties of impurities, particularly cyclohexane, are produced in addition to the desired cyclohexylbenzene. These impurities represent loss of valuable benzene feed and, unless removed, build up in the benzene recycle stream thereby displacing benzene and further increasing the production of undesirable by-products. To address this problem, it has been proposed to contact the cyclohexane with a dehydrogenation catalyst under conditions to selectively convert cyclohexane to benzene, which can then be recycled to the hydroalkylation process. See, for example, U.S. Pat. No. 7,579,511 and International Patent Publication No. WO2009/131769.

Benzene hydroalkylation consumes hydrogen and, although cyclohexane dehydrogenation produces hydrogen, controlling catalyst aging requires that hydrogen is co-fed with the cyclohexane to the dehydrogenation process. Also, the amount of hydrogen consumed in the benzene hydroalkylation process far outweighs the amount of hydrogen produced in the cyclohexane dehydrogenation process. As a result fresh hydrogen must always be introduced in the hydroalkylation/dehydrogenation loop. According to the invention, it has now been found that (1) the life of the hydroalkylation catalyst can be prolonged by contacting the hydrogen stream with the dehydrogenation catalyst prior to the hydroalkylation step; and (2) the selection of the point in this loop where the hydrogen is introduced has a profound effect on efficacy of the entire process, namely the useful life of the catalysts and the amount of benzene recycle can be increased and the formation of certain byproducts, such as bicyclohexane, can be decreased.

SUMMARY

Accordingly, the invention resides in one aspect in a process for cyclohexylbenzene, the process comprising:

(a) contacting benzene with hydrogen in the presence of a hydroalkylation catalyst under hydroalkylation conditions effective to form a first effluent stream comprising cyclohexylbenzene, cyclohexane, and benzene; and (b) contacting at least a portion of the cyclohexane from the first effluent stream with hydrogen in the presence of a dehydrogenation catalyst under dehydrogenation conditions effective to convert at least some of the cyclohexane into benzene contained in a second effluent stream, wherein at least some of the hydrogen-containing stream is supplied to said dehydrogenation reaction zone before contacting said hydroalkylation catalyst in (a).

In one embodiment, the process further comprises:

(c) contacting the first effluent stream with hydrogen to separate the first effluent stream into a vapor-phase stream containing cyclohexane and benzene and a liquid-phase stream containing cyclohexylbenzene.

Conveniently, at least some of the hydrogen in (c) described above contacts the dehydrogenation catalyst before contacting the first effluent stream.

Conveniently, at least a portion of said first effluent stream is fed to a gas/liquid separator to recover at least a portion of the cyclohexylbenzene prior to the contacting it with a dehydrogenation catalyst in the contacting step (b) described above.

Conveniently, at least a portion of the vapor phase stream is recycled to the contacting (a).

Generally, the hydrogen is supplied in a direction countercurrent to the first effluent stream.

In one embodiment, the hydrogen is contacted with the first effluent stream in a stripper located downstream of the contacting step (a).

In another embodiment, the contacting (a) is conducted in a plurality of series connected reaction zones and the hydrogen is supplied at or adjacent the outlet of the final reaction zone.

In a further aspect, the invention resides in a process for producing cyclohexylbenzene, the process comprising:

(a) contacting benzene with hydrogen in the presence of a hydroalkylation catalyst under hydroalkylation conditions effective to form a first effluent stream comprising cyclohexylbenzene, cyclohexane, and benzene;

(b) supplying hydrogen to the process such that said first effluent stream is a mixed gas and liquid phase stream, wherein at least a portion of the cyclohexane and benzene is in the vapor phase; and (c) separating the first effluent stream into a vapor phase stream containing cyclohexane and benzene, and a liquid phase stream containing cyclohexylbenzene.

Generally, at least a portion of the vapor phase stream containing cyclohexane and benzene is contacted with hydrogen in the presence of a dehydrogenation catalyst under dehydrogenation conditions effective to convert at least a portion of the cyclohexane to benzene.

In one embodiment, the hydrogen is supplied to the process such that the fresh hydrogen contacts said dehydrogenation catalyst before contacting said hydroalkylation catalyst in (a).

Conveniently, part of the vapor phase stream is recycled to the contacting (a).

Preferably, the hydroalkylation catalyst comprises at least one molecular sieve and at least one hydrogenation metal, wherein the at least one molecular sieve is selected from zeolite beta, mordenite, zeolite X, zeolite Y, and a molecular sieve of the MCM-22 family.

BRIEF DESCRIPTION OF THE DRAWINGS

FIG. 1 is a schematic drawing of part of an integrated process for producing phenol from benzene according to one embodiment of the invention.

DETAILED DESCRIPTION OF THE EMBODIMENTS

Described herein is a process for producing cyclohexylbenzene by the hydroalkylation of benzene, followed by the dehydrogenation of the cyclohexane by-product to produce additional benzene that can be recycled to the hydroalkylation step. In particular, it has now been found that, by supplying hydrogen to the system such that the hydrogen contacts the dehydrogenation zone (e.g., the dehydrogenation catalyst) before contacting the hydroalkylation catalyst, the useful life of both catalysts can be increased. Although the reason for this advantage is not fully understood, it is believed that the dehydrogenation reaction removes certain contaminants in the hydrogen feed that could have an adverse effect on the hydroalkylation catalyst. For example, the hydrogen feed may contain one or more impurities such carbon monoxide and oxygenates (e.g., an aldehydes and/or ketones), which are at least partially removed through contact with the dehydrogenation catalyst. In one embodiment, at least 5 wt %, or at least 10 wt %, or at least 25 wt %, or at least 50 wt % of one or more impurities are removed from the hydrogen feed based upon the weight of the feed.

In addition, it is found that supplying the hydrogen at or adjacent the outlet of the hydroalkylation reactor (in the case of a single reactor system) or the last hydroalkylation reactor (in the case of a multiple reactor system) facilitates separation of benzene from the reaction effluent for recycle to the hydroalkylation step, thereby improving process efficiency and increasing product selectivity. For example, the hydroalkylation effluent may be contacted with hydrogen to separate it into a vapor-phase stream containing cyclohexane and benzene and a liquid-phase stream containing cyclohexylbenzene. In one embodiment, the hydrogen is contacted with the hydroalkylation effluent in a countercurrent manner. At least a portion of the hydrogen may be contacted with the dehydrogenation catalyst before being supplied to the outlet or hydroalkylation reactor.

In an embodiment, hydrogen is contacted with the hydroalkylation effluent in a stripper device located downstream of the hydroalkylation reactor(s).

In an embodiment, the hydroalkylation effluent is fed to a gas/liquid separator to recover at least a portion of the cyclohexylbenzene prior to contact with the dehydrogenation catalyst.

In one embodiment, benzene is contacted with hydrogen in the presence of a hydroalkylation catalyst under hydroalkylation conditions effective to form a first effluent stream comprising cyclohexylbenzene, cyclohexane, and benzene. Hydrogen is supplied to the process such that the first effluent stream is a mixed gas and liquid phase stream and at least a portion of the cyclohexane and benzene are in the vapor phase. The first effluent stream is separated into a vapor phase stream containing cyclohexane and benzene, and a liquid phase stream containing cyclohexylbenzene. The vapor phase stream containing hydrogen may be contacted with a dehydrogenation catalyst under dehydrogenation conditions to convert at least a portion of the cyclohexane to benzene. A portion of the vapor phase stream may be recycled to the hydroalkylation step.

In one preferred embodiment, the present process forms part of an integrated process for producing phenol from benzene in which the cyclohexylbenzene produced in the benzene hydroalkylation reaction is oxidized to produce cyclohexylbenzene hydroperoxide and the hydroperoxide is cleaved to produce phenol and cyclohexanone. The ensuing description will therefore focus on this integrated process.

Production of the Cyclohexylbenzene

One step of the integrated process for producing phenol is the selective hydrogenation of benzene in the presence of a bifunctional hydroalkylation catalyst. The hydroalkylation reaction produces cyclohexylbenzene (CHB) according to the following reaction:

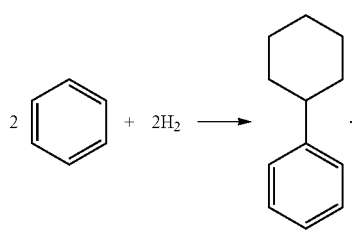 [SMILES: c1ccccc1 ; c1ccc(C2CCCCC2)cc1]

Any commercially available benzene feed can be used in the hydroalkylation reaction, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically, the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones optionally connected in series (e.g., three reaction zones), in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve and a hydrogenation metal.

Suitable molecular sieves for use in the hydroalkylation catalyst include zeolite beta, mordenite, zeolite X, zeolite Y, and a molecular sieve of the MCM-22 family, with MCM-22 family material being preferred. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56, and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27, (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Treatment of the Cyclohexylbenzene Product

Although the hydroalkylation reaction using an MCM-22 family zeolite catalyst is highly selective towards cyclohexylbenzene, the hydroalkylation reaction will inevitably produce certain by-products. As stated previously, a prevalent by-product is normally cyclohexane but generally the reaction effluent will also contain dicyclohexylbenzene, tri-cyclobenzene and even heavier alkylates.

In the present process, the cyclohexane by-product is removed from the hydroalkylation reaction effluent by initially fractionating the reaction effluent into a $C_6$-rich fraction and a heavy fraction and then subjecting the $C_6$-rich fraction to dehydrogenation to convert the cyclohexane to additional benzene that can be recycled to the hydroalkylation step. In this respect, it is to be appreciated that when a composition is described herein as being "rich in" or "enriched" in a specified species, it is meant that the wt % of the specified species in that composition is greater than the feed composition (i.e., the input).

The dehydrogenation process is conducted by contacting at least a portion of the hydroalkylation reaction effluent with a dehydrogenation catalyst under dehydrogenation conditions comprising a temperature between 200° C. and 550° C. and a pressure between 100 kPa and 7,000 kPa. Typically the dehydrogenation catalyst comprises (i) 0.05 wt % to 5 wt % of a metal selected from Group 14 of the Periodic Table of Elements, such as tin; and (ii) 0.1 wt % to 10 wt % of a metal selected from Groups 6 to 10 of the Periodic Table of Elements, such as platinum or palladium, the wt % s based upon total weight of the dehydrogenation catalyst. In addition, the dehydrogenation catalyst further comprises a support which is typically selected from the group consisting of silica, alumina, a silicate, an aluminosilicate, zirconia, carbon, and carbon nanotubes.

The dehydrogenation catalyst is typically prepared by sequentially or simultaneously treating the support, such as by impregnation, with one or more liquid compositions comprising the Group 6-10 metal or a precursor thereof, the Group 14 metal or a precursor thereof and/or the optional inorganic base component or a precursor in a liquid carrier, such as water. An organic dispersant may be added to each liquid carrier to assist in uniform application of the metal component(s) to the support. Suitable organic dispersants include amino alcohols and amino acids, such as arginine. Generally, the organic dispersant is present in the liquid composition in an amount between 1 wt % and 20 wt % of the liquid composition.

In one preferred embodiment, the catalyst is prepared by sequential impregnation with the Group 14 metal component being applied to the support before the Group 6-10 metal component.

After treatment with the liquid composition, the support is heated in one or more stages, generally at a temperature of 100° C. to 700° C. for a time of 0.5 to 50 hours, to effect one or more of: (a) removal of the liquid carrier; (b) conversion of a metal component to a catalytically active form; and (c) decompose the organic dispersant. The heating may be conducted in an oxidizing atmosphere, such as air, or under reducing atmosphere conditions, such as hydrogen. After treatment with a liquid composition, the support is generally heated at a temperature of 200° C. to 500° C., such as 300° C. to 450° C., for a time of 1 to 10 hours.

In one embodiment, the dehydrogenation catalyst has an oxygen chemisorption value of greater than 5%, such as greater than 10%, for example greater than 15%, even greater than 20%, greater than 25%, or even greater than 30%. As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]*100%. The oxygen chemisorption values referred to herein are measured using the following technique. Oxygen chemisorption measurements are obtained using the Micromeritics ASAP 2010. Approximately 0.3 to 0.5 grams of catalyst are placed in the Micrometrics device. Under flowing helium, the catalyst is ramped from ambient temperature (i.e., 18° C.) to 250° C. at a rate of 10° C. per minute and held for 5 minutes. After 5 minutes, the sample is placed under vacuum at 250° C. for 30 minutes. After 30 minutes of vacuum, the sample is cooled to 35° C. at 20° C. per minute and held for 5 minutes. The oxygen and hydrogen isotherm is collected in increments at 35° C. between 0.50 and 760 mm Hg. Extrapolation of the linear portion of this curve to zero pressure gives the total (i.e., combined) adsorption uptake.

Preferably, the alpha value of the dehydrogenation catalyst is from 0 to 10, and from 0 to 5, and from 0 to 1. The alpha value of the support is an approximate indication of the catalytic cracking activity of the catalyst compared to a standard catalyst. The alpha test gives the relative rate constant (rate of normal hexane conversion per volume of catalyst per unit time) of the test catalyst relative to the standard catalyst which is taken as an alpha of 1 (Rate Constant=0.016 sec$^{-1}$). The alpha test is described in U.S. Pat. No. 3,354,078 and in J.

Catalysis, 4, 527, (1965); 6, 278, (1966); and 61, 395, (1980), to which reference is made for a description of the test. The experimental conditions of the test used to determine the alpha values referred to in this specification include a constant temperature of 538° C. and a variable flow rate as described in detail in J. Catalysis, 61, 395, (1980).

The dehydrogenation process is conducted in the presence of hydrogen, typically such that hydrogen to hydrocarbon feed molar ratio is between about 0.5 to about 20. In the present process, the hydrogen is supplied to the system so that some and preferably all the hydrogen contacts the dehydrogenation catalyst before contacting the hydroalkylation catalyst. This is generally achieved by supplying make-up hydrogen to, or downstream of, the outlet of the hydroalkylation reactor (in the case of a single reactor system) or the last hydroalkylation reactor (in the case of a multiple reactor system).

In one embodiment the hydrogen is supplied to a stripper located downstream of the hydroalkylation catalyst so as to contact the reactor effluent flowing through the stripper countercurrent to the hydrogen. The hydrogen lowers the pressure of the reactor effluent causing the effluent to separate into a vapor-phase stream rich in cyclohexane and benzene and a liquid-phase stream rich in cyclohexylbenzene. Part of the vapor phase stream is removed from the reaction effluent and recycled to the hydroalkylation process, whereas the remainder of the reaction effluent is fractionated into a $C_6$-rich fraction and a heavy fraction.

This heavy fraction is further fractionated to produce a $C_{12}$-rich fraction containing most of the cyclohexylbenzene and a $C_{18}$-rich fraction containing most of the dicyclohexylbenzene. The cyclohexylbenzene is fed to the oxidation step discussed below whereas, depending on the amount of the dicyclohexylbenzene produced, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 hr$^{-1}$ to about 10 hr$^{-1}$ on total feed, and a benzene/dicyclohexylbenzene weight ratio about of 1:1 to about 5:1. The transalkylation reaction can, and typically will, generate, additional methylcyclopentane.

Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as WO$_x$/ZrO$_2$, phosphoric acid, sulfated zirconia and mixtures thereof. Generally, the acid catalyst includes at least one aluminosilicate, aluminophosphate or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction typically is from 0 to about 0.9, such as from about 0.01 to about 0.5.

Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

It is to be appreciated that the transalkylation and dealkylation reactions can, and typically will, generate additional methylcyclopentane and hence the products of these reactions can be subjected to the separation steps described above to generate the $C_6$ fraction(s), which may subsequently be subjected to dehydrogenation.

Cyclohexylbenzene Oxidation

In order to convert the cyclohexylbenzene into phenol and cyclohexanone, the cyclohexylbenzene may be oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % oxygen in air through membrane enrichment of air, cryogenic separation of air or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo [2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and cyclohexylbenzene. For example, the oxidation reaction effluent may include cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent may be subjected to a cleavage reaction, with or without undergoing any prior separation or treatment. For example, all or a fraction of the oxidation reaction effluent may be subjected to high vacuum distillation to generate a product enriched in cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Publication No. WO 2009/025939.

Hydroperoxide Cleavage

Another reactive step in the conversion of the cyclohexylbenzene into phenol and cyclohexanone involves the acid-catalyzed cleavage of the cyclohexyl-1-phenyl-1-hydroperoxide produced in the oxidation step.

Generally, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to no greater than 3000 wppm, or at least 150 wppm to no greater than 2000 wppm of the acid catalyst, or at least 300 wppm to no greater than 1500 wppm of the acid catalyst, based upon total weight of the cleavage reaction mixture.

In other embodiments, a heterogeneous acid catalyst is employed for the cleavage reaction, such as molecular sieve, and in particular a molecular sieve having a pore size in excess of 7 Å. Examples of suitable molecular sieves include zeolite beta, zeolite Y, zeolite X, ZSM-12 and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Generally, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon 6 and nylon 6,6.

The phenol produced through the processes disclosed herein may be used, for example, to produce phenolic resins, bisphenol A, ε-caprolactam, adipic acid and/or plasticizers.

The invention will now be more particularly described with reference to the accompanying drawings and the following non-limiting examples.

Referring to the drawings, FIG. 1 illustrates part of an integrated process for producing phenol according to a first embodiment of the invention. In this process hydrogen from line 11 is mixed with benzene from line 12 and the resultant mixed stream is heated by heat exchangers 13 before being fed to the first of three vertically disposed, series-connected hydroalkylation reactors 14. Each of the reactors 14 contains a bed of hydroalkylation catalyst and is operated under conditions such that benzene and hydrogen in the feed react to produce cyclohexylbenzene together with the by-products discussed above.

The hydroalkylation reaction product exiting the final reactor 14 is composed mostly of cyclohexylbenzene, dicyclohexylbenzene, cyclohexane, and benzene. After it exits the final reactor 14, this product flows downwardly through a stripper 16 and contacts make-up hydrogen which is fed by line 17 to the bottom of the final reactor 14 and flows upwardly through the stripper. The introduction of the hydrogen lowers the pressure of the reaction product so that it separates into a vapor-phase stream, which contains hydrogen, cyclohexane, and benzene and which exits the reactor through line 18, and a liquid-phase stream, which contains cyclohexylbenzene and dicyclohexylbenzene and which exits the reactor through line 19.

The vapor phase stream in line 18 is cooled and fed to a vapor/liquid separator 21 where part of the stream, composed mainly of benzene, recondenses and is recycled by line 22 to the benzene supply line 12. The remainder of the vapor phase stream is removed from the separator by line 23 and mixed with the liquid phase stream in line 19. The resultant mixed stream is fed to a distillation column 24 where an overhead stream containing hydrogen and most of the cyclohexane and benzene hydroalkylation reaction product is removed and fed by line 25 to a dehydrogenation reactor 26. The bottoms product from the first distillation column 24 contains most of the cyclohexylbenzene and dicyclohexylbenzene in the hydroalkylation reaction product and is removed via line 27 for recovery of the cyclohexylbenzene.

The dehydrogenation reactor 26 converts the cyclohexane in the overhead stream to benzene and the effluent from the dehydrogenation reactor 26 is fed by line 30 to a further fractionator 28 for separation of the benzene for eventual recycle of the benzene to the reactors 14. Hydrogen exiting dehydrogenation reactor 26 via line 31 may be recycled to reactors 14, optionally via combination with the hydrogen in line 11.

The invention claimed is:

1. A process for producing cyclohexylbenzene, the process comprising:
   (a) contacting benzene with a hydrogen-containing stream in the presence of a hydroalkylation catalyst under hydroalkylation conditions effective to form a first effluent stream comprising cyclohexylbenzene, cyclohexane, and benzene;
   (b) contacting the first effluent stream with a make-up hydrogen stream to separate the first effluent stream into a vapor-phase stream comprising hydrogen, cyclohexane, and benzene, and a liquid-phase stream comprising cyclohexylbenzene;
   (c) contacting at least a portion of the vapor-phase stream comprising hydrogen, cyclohexane, and benzene with a dehydrogenation catalyst in a dehydrogenation reaction zone under dehydrogenation conditions effective to convert at least a portion of the cyclohexane into benzene and produce a second effluent stream comprising benzene and a hydrogen recycle stream; and
   (d) recycling the hydrogen recycle stream to step (a) to form at least a portion of the hydrogen-containing stream.

2. The process of claim 1, wherein the make-up hydrogen stream comprises at least one impurity selected from carbon monoxide and an oxygenate, and at least a portion of the impurity is removed through contact with said dehydrogenation catalyst prior to step (d).

3. The process of claim 2, wherein at least 10 wt % of the impurity is removed based on weight of the make-up hydrogen stream.

4. The process of claim 2, wherein the impurity is carbon monoxide.

5. The process of claim 2, wherein the oxygenate is an aldehyde or a ketone.

6. The process of claim wherein at least a portion of the make-up hydrogen stream contacts the dehydrogenation catalyst before contacting the first effluent.

7. The process of claim 1, wherein the first effluent is separated in a gas/liquid separator and at least a portion of the cyclohexylbenzene in the liquid phase is recovered.

8. The process of claim 1, wherein at least a portion of the vapor-phase stream is recycled to step (a).

9. The process of claim 7, wherein said make-up hydrogen stream is supplied in a direction countercurrent to the first effluent.

10. The process of claim 1, wherein the make-up hydrogen stream is contacted with the first effluent stream in a stripper located downstream of step (a).

11. The process of claim 1, wherein step (a) is conducted in a plurality of reaction zones connected in series and the make-up hydrogen stream is supplied at or adjacent to the outlet of the final reaction zone.

12. The process of claim 1, wherein the contacting step (a) is conducted in three series reaction zones connected in series.

13. The process of claim 1, wherein the hydroalkylation catalyst comprises at least one molecular sieve and at least one hydrogenation metal.

14. The process of claim 13, wherein the at least one molecular sieve is selected from zeolite beta, mordenite, zeolite X, zeolite Y, and a molecular sieve of the MCM-22 family.

15. A process for producing cyclohexylbenzene, the process comprising:
   (a) contacting benzene with hydrogen in the presence of a hydroalkylation catalyst under hydroalkylation conditions effective to form a first effluent stream comprising cyclohexylbenzene, cyclohexane, and benzene;
   (b) contacting said first effluent stream with a make-up hydrogen stream such that said first effluent stream is a mixed gas and liquid phase stream, wherein at least a portion of the cyclohexane and benzene is in the vapor phase; and
   (c) separating the first effluent stream into a vapor-phase stream comprising hydrogen, cyclohexane, and benzene, and a liquid-phase stream comprising cyclohexylbenzene.

16. The process of claim 15, wherein at least a portion of the vapor phase stream comprising hydrogen, cyclohexane, and benzene contacts a dehydrogenation catalyst under dehydrogenation conditions effective to convert at least a portion of the cyclohexane to benzene and produce a dehydrogenation effluent comprising benzene and hydrogen.

17. The process of claim 16, wherein the make-up hydrogen stream contacts said dehydrogenation catalyst before contacting said first effluent and at least a portion of the hydrogen in the dehydrogenation effluent is recycled to step (a).

18. The process of claim 15, wherein at least part of the vapor phase stream is recycled to step (a).

19. The process of claim 15, wherein the hydroalkylation catalyst comprises at least one molecular sieve and at least one hydrogenation metal.

20. The process of claim 19, wherein the at least one molecular sieve is selected from zeolite beta, mordenite, zeolite X, zeolite Y, and a molecular sieve of the MCM-22 family.

* * * * *